(12) United States Patent
Liu

(10) Patent No.: US 8,354,108 B2
(45) Date of Patent: Jan. 15, 2013

(54) FULLY HUMAN ANTIBODY TO HUMAN TNFα, MOLECULAR EVOLUTION AND USE THEREOF

(76) Inventor: Qingfa Liu, Shanghai (CN)

( * ) Notice: Subject to any disclaimer, the term of this patent is extended or adjusted under 35 U.S.C. 154(b) by 45 days.

(21) Appl. No.: 13/008,015

(22) Filed: Jan. 18, 2011

(65) Prior Publication Data

US 2011/0182906 A1 Jul. 28, 2011

Related U.S. Application Data

(63) Continuation-in-part of application No. PCT/CN2009/070938, filed on Mar. 20, 2009.

(51) Int. Cl.
*A61K 39/395* (2006.01)
*C07K 16/24* (2006.01)
*C07K 14/525* (2006.01)

(52) U.S. Cl. .................. 424/145.1; 530/388.23

(58) Field of Classification Search .................. None
See application file for complete search history.

(56) References Cited

U.S. PATENT DOCUMENTS

| | | |
|---|---|---|
| 7,109,320 B2 | 9/2006 | Kang |
| 7,196,177 B2 | 3/2007 | Kang |
| 7,285,269 B2 | 10/2007 | Babcook |
| 2005/0049402 A1 | 3/2005 | Babcook |
| 2005/0124041 A1 | 6/2005 | Kang |
| 2006/0147452 A1 | 7/2006 | Kang |
| 2008/0008703 A1 | 1/2008 | Yoo |
| 2008/0187531 A1 | 8/2008 | Babcook |

FOREIGN PATENT DOCUMENTS

| | | |
|---|---|---|
| CN | 1613874 A | 5/2005 |
| CN | 1778921 A | 5/2006 |
| WO | WO2004050683 A2 | 6/2004 |
| WO | WO2008141511 A8 | 11/2008 |

OTHER PUBLICATIONS

International Search Report PCT/CN2009/070938.
By-passing Immunization—Human Antibodies from V-gene Libraries Displayed on Phage; Marks, James D. et al.; J. Mol. Biol. 222:581-597 (1991).
By-passing Immunization Human Antibodies from Synthetic Repertoires of Germline VH Gene Segments Rearranged in Vitro; Hennie R. Hoogenboom and Greg Winter; J. Mol. Biol. 227:381-388 (1992).
Recombinant human antibody single chain variable fragments reactive with *Candida albicans* surface antigens; Haidaris, Constantine G. et al.; Journal of Immunological Methods 257:185-202 (2001).
Isolation of high affinity human antibodies directly from large synthetic repertoires; Griffiths, Andrew D. et al.; The EMBO Journal vol. 13 No. 14 pp. 3245-3260; (1994).
Antibody fragments from a 'single pot' phage display library as immunochemical reagents; Nissim, Ahuva; The EMBO Journal vol. 13 No. 3 pp. 692-698 (1994).

*Primary Examiner* — David Romeo
(74) *Attorney, Agent, or Firm* — Cittone & Chinta LLP; Henry J. Cittone

(57) ABSTRACT

The present invention relates to the discovery and improvement of proteins that can specifically bind with human TNFa (Tumor Necrosis Factor alpha), the proteins are full human anti human TNFa monoclonal antibodies derived from human B cells. This invention disclosed the anti human TNFa monoclonal antibodies, their amino acid sequence of light chain comprising SEQ ID NO:8, and that of heavy chain comprising SEQ ID NO:16 or SEQ ID NO:18. This invention disclosed the coding genes of these antibodies, their Fab molecules, and their potential application to treat clinically the diseases related to TNFa, such as inflammation diseases.

6 Claims, 4 Drawing Sheets

FULLY HUMAN ANTIBODY TO HUMAN TNFα, MOLECULAR EVOLUTION AND USE THEREOF

CROSS-REFERENCES TO RELATED APPLICATIONS

The present application is a Continuation-In-Part of PCT Application No. PCT/CN2009/070938 filed on Mar. 20, 2009, disclosure of which is incorporated herein by reference in its entirety.

FIELD OF THE INVENTION

This invention is related to biotechnology, in particular to anti human TNFα monoclonal antibodies, their improvement via molecular evolution, and their clinical application after improvement.

BACKGROUND OF THE INVENTION

About Autoimmune Diseases

Autoimmune diseases represented by Rheumatoid arthritis, are serious diseases that affect human health worldwide. Until bio-antagonists such as TNFα Receptor Inhibitor/Fc protein, therapeutic monoclonal antibodies, were introduced into clinical application, the first line treatment for autoimmune diseases had been COX2 inhibitors, such as Fosamax abroad, and some Chinese medicines in China. All these chemicals are far from good in efficacy or safety or both. After monoclonal antibody or monoclonal antibody like products approval by FDA from 1997, several TNFα bioblockers were approved to be used in autoimmune disease therapy and gained great success, and resulted in fierce competition in development of TNFα bioinhibitors all over the world. Up to now, at least five TNFα bioinhibitors have been introduced into the market, such as Enbrel, Remicade, Humira, Simponi and Cimzia for Rheumatoid, and Amivive, Raptiva, Enbrel for Psoriasis. Among them, Enbrel, Remicade and Humira, etc, had been tested for clinical treatment of other autoimmune diseases.

Physiological Functions of TNFα

TNFα is a major inflammatory cytokine that was first identified for its ability to induce rapid hemorrhagic necrosis of experimental cancers. Beside this it has multiple functions including regulatory role in inflammation addressed in later research. It was shown that its precursor consists of 233 amino acids including a 76 amino acid peptide at N-end, which is not a signal peptide but an anchor holding the matured secretory molecules onto the cell membrane. The matured mRNA molecule coding this precursor is 1.7 kb in length produced mainly in mononuclear phagocyte. Matured TNFα is composed of 157 amino acids linked together by two disulfide bonds, and has not glycosylation site. TNFα has different functions to different cells, such as killing cells, accelerating or suppressing cell growth. It can suppress hematopoiesis thereby causing red cell reduction and resulting in activation of macrophagocyte and killing function, enhancing macrophagocyte's immune response and neutrophilic granulocyte accumulation around inflammatory sites. It can inhibit B cell response to EBV and inhibit B cell proliferation and immunoglobulin secretion. It can cause tumor hemorrhagic necrosis via affecting tumor vessels resulting in cancer growth inhibition, and improve anti cancer ability of human body by enhancing immunoreaction. In addition, this factor has important physiological functions in liver, bone, muscle, blood vessel and others.

TNFα has close relationship with autoimmune diseases. TNFα over expression in diseased sites is the key cause of swell and pain, and TNFα is the closest factor in TNF family related to autoimmune diseases.

It was found that TNFα overexpression has close relationship with occurrence and development of multiple inflammatory diseases, including but not limited to Rheumatoid arthritis, Psoriasis vulgaris, Systemic Lupus erythematosus, Ankylosing spondylitis, multiple sclerosis. Therefore, any antagonist that down-regulate TNFα level, including but not limited to monoclonal antibodies and soluble receptors, were effective in the treatment of the above diseases. There were several monoclonal antibodies and soluble receptors successfully applied in autoimmune disease treatment such as the famous products Enbrel, Remicade and Humira. Extensive clinical application showed that they were of prominent efficacy with high safety for various autoimmune diseases. These results indicated that TNFα was a very ideal target for autoimmune disease treatment.

Rheumatoid arthritis (shortly RA) is a very common autoimmune disease with swollen joint swell and other joint problems, and about 20% of the patients would become joint or bone injured, or even disabled. This will lead to not only economic problems to the family and society, but also very bad daily life to the patients.

Psoriasis is another common autoimmune disease that causes skin redness and irritation. Skin cells grow deep in the skin and normally rise to the surface about once a month. In persons with Psoriasis, this process is too fast so that dead skin cells build up on the skin surface leading to inflammation, swell, and thick and red skin with flaky, silver-white patches or even serious festers. These symptoms mostly appear on scalp, knees, elbows and trunk, and may affect people of any age, any nationality and both sexes equally. The serous fester will not only leave the patients a lot of trouble for daily therapy and prognosis, but also let the patients bear heavy psychological burden because it is queasy and recognized by common people as an infectious disease so that they are excluded from the surrounding population. This disorder gives a lot of difficulties for daily life and mentality to the patients. If appropriate treatment is not applied in time, psoriasis will develop into psoriasis arthritis and lead to disabled.

Autoimmune diseases with the same pathogenesis include Ankylosing spondylitis (AS). AS patients exhibit spondyle joints injured, which often leads to not only movement restriction, disabled, or even complete loss of self-care ability in daily life, but also to serious physical torture.

Monoclonal Antibodies, Therapeutic Monoclonal Antibodies and their Development In the last two decades, therapeutic monoclonal antibody experienced a great progress and achievement. There have been several heavyweight products successfully developed and marketed. Among them, there have been at least Enbrel, Humira and Remicade targeting to TNFα and Rituxan targeting to CD20. All these therapeutic monoclonal antibodies represented prominent curative effect, and made tremendous success in both technology and business so that they rapidly become into first-line therapy. Therapeutic monoclonal antibodies gained an unprecedented success in treatment of cancers, some infectious diseases and so on. Because of their prominent curative effect and the huge market demand created by this, therapeutic monoclonal antibodies are still under extensive development.

Presently, the most popular method to obtain monoclonal antibodies is hybridoma technology, in which rodents such as mice and rabbits, poultry such as chicken and primates such as macaques and apes, human beings and so on are involved. In addition, more and more studies on camel antibody have been reported, and humanized mice have been taken as a powerful tool in novel therapeutic monoclonal antibody development.

Monoclonal antibodies used in therapy requires many, among them the interconnected factors such as affinity, neutralization ability, specificity and side-effects, are the main considerations. Generally speaking, a higher affinity will lead to lower effective dosage, and further result in lower manufacturing cost and less side-effects. A higher specificity will lower the effects on other components in vivo, and further result in less side effects. Hence, it is a very important aspect to obtain monoclonal antibodies with high affinity. At the same time, not all current methods can produce monoclonal antibodies that meet the pharmaceutical requirements in both affinity and neutralization ability.

It is not easy to obtain a monoclonal antibody that is good enough for therapy although there have been many methods to produce monoclonal antibodies. In many cases, limitations in specificity, neutralization ability, affinity and/or others can be an obstacle for a monoclonal antibody to be successfully used in clinical therapy.

Another important factor that determines a monoclonal antibody's usability in clinical therapy is whether it can be easily manufactured. This requires that the said monoclonal antibody can be manufactured in large scale with low cost. The most important indicator for this is the amount of the product in a liter media, this is normally called specific productivity.

In the last two decades, great success was achieved with recombinant therapeutic monoclonal antibodies. New products emerged in endlessly. Recombinant therapeutic monoclonal antibodies have became in therapeutic medicines the field that developed most rapidly, and have drawn great attention from the industry. Governments and pharmaceutical companies invested actively at a large scale to develop therapeutic monoclonal antibody medicines. However, many difficulties came forth while therapeutic monoclonal antibody technology developed rapidly. Outstanding ones of them include that recombinant mammalian cells must be used for their production, and their dosages are massive. This leads to high cost that patients could not bear. Therefore, how to reduce the costs while ensuring their curative effect became a key problem for monoclonal antibody medicine development.

The dramatic selling increase of marketed monoclonal antibody medicines and durative introduction of more and more new products into market challenge manufacturers' productivity.

TNFα Antagonists and their Clinical Applications

As mentioned above, TNFα is a key factor that leads to swell and pain in joints of RA patients. On the other hand, it is also the key mediator in septic shock, Ankylosing spondylitis, psoriasis and rheumatoid arthritis as indicated in many studies. The increased TNFα level in the serum of septic shock and RA patients is an indicator of the increased mortality and disability rate. Passive input of TNFα antagonists can prevent septic shock and tissue lesion caused by LPS and bacteria infection. Clinical application of TNFα monoclonal antibodies or its receptors shows notable curative effect for septic shock, Ankylosing spondylitis, Psoriasis and Rheumatoid arthritis.

Up to now, there are multiple kinds of several monoclonal antibodies and receptor-Fc fusion proteins against human TNFα that have been successfully applied in clinic to the above indications, and gained a great success in industrialization.

Humira is a therapeutic monoclonal antibody developed by Abbot targeting human TNFα, which was approved by FDA in 2002. Its first approved indication was RA. Because of its prominent efficacy, the global year sale reached as high as 2 billion US dollars in 2006. Its variable regions and the corresponding coding DNA sequences were from a fully human antibody library constructed by CAT, and its Fc coding region was from human IgG1. It can be seen from this that the variable regions of this product were not directly from human being but from an antibody library derived from human B cells.

The present invention uses the lymphocytes separated from peripheral blood of a RA patient as the starting material, antibody library technology as the core to obtain Fab format molecules of ful human antibodies being able to neutralize human TNFα after a serial panning. Molecular evolution technology is used to improve or alter the affinity and specificity of the said molecules to meet requirements for therapeutic monoclonal antibodies. The full length molecules with biologic activity are successfully expressed in a CHO cell line. Therefore, the amino acid sequences and their corresponding DNA sequences in this invention are from human being. The affinity of the anti human TNFα monoclonal antibodies in this invention is notably higher than Humira, and the clinically effective dosages are significantly reduced.

SUMMARY

An object of this invention is to disclose an anti human TNFα monoclonal antibody and its corresponding coding DNA sequences.

Another object of this invention is to disclose possible pharmaceutical applications of the said anti human TNFα monoclonal antibody.

One aspect of this invention discloses an anti human TNFα monoclonal antibody the light chain amino acid sequence of which is set forth in SEQ ID NO:8, and the heavy chain amino acid sequence of which is set forth in SEQ ID NO:9 or SEQ ID NO: 10. Preferably, the anti human TNFα full length heavy chain amino acid sequence comprise the poly peptide as set forth in SEQ ID NO:16 or SEQ ID NO: 18. The above said SEQ ID NO:8 is a light chain variable region amino acid sequence.

Another aspect of this invention discloses a polynucleotide coding the light chain of the above said anti human TNFα monoclonal antibody. More preferably, this polynucleotide comprises SEQ ID NO:5.

The third aspect of this invention discloses a polynucleotide coding the full length heavy chain of the above said anti human TNFα monoclonal antibody. More preferably, this polynucleotide comprises SEQ ID NO:15 or SEQ ID NO:17.

The forth aspect of this invention discloses the Fab format of the above said anti human TNFα monoclonal antibody.

The fifth aspect of this invention discloses the application of the above said anti human TNFα monoclonal antibody or its Fab format in manufacturing the formulation used for treatment of inflammation related to TNFα, such as manufacturing a medicine applicable to treat RA. The Dosage and method of using the said anti human TNFα monoclonal antibody or its Fab format thereof could be determined with reference to the conventional methods for existing TNFα antibodies.

Advantages and Benefits

Although existing anti TNFα monoclonal antibody like medicines are deemed to have better efficacy compared with any other medicines, they have still obvious disadvantages. Firstly, they are mainly expressed and purified by the aid of mammalian cell lines, in which the gene expression level was relatively low and the production capacity is far from ideal to meet the market requirement. This problem still exists even though the volume of a single bioreactor is over 20000 liters as constructed with 500 million US dollars by Amgen. Secondly, the high cost rejects a large part of patients outside of treatment. As estimated, it would cost 11400, 14200 and 16776 US dollars a year for a patient to treat RA using Enbrel, Remicade and Humira respectively. At the same time, the treatment would last for a long period. Thirdly, these antibodies contain Fc fragment that (it) is of complement fixation, ADCC and other bioactivities, so that their application in vivo could lead to apoptosis of the cells that express TNFα. And fourthly, products like Remicade are human-mouse chimeric monoclonal antibodies, of whose components one-third is mouse-homologous. This would trigger HAMA reaction to these chimeric structures in more than 10% patients who applied this drug continually, and this would in turn lower their efficacy and induce serious adverse reactions. The coming product CDP870, a PEGylated humanized anti human TNFα Fab format in whose mouse-homologous is as low as 10%, is still of immunogenicity.

Fully human monoclonal antibodies against human TNFα are obtained in the present invention via human-human hybridoma technology. Primary physical, chemical and biological analysis shows that these monoclonal antibodies have high affinity to TNFα, and ability to neutralize effectively the killing effect of TNFα on the cell line L929 in vitro. Firstly, the obtained monoclonal antibodies are of the lowest immunogenicity on human body as their amino acid sequences are completely identical to monoclonal antibodies produced by and in a human body. Secondly, *Escherichia coli* could be used to manufacture their Fab format so that the costs would be reduced dramatically, and more importantly, all side effects caused by complement fixation and ADCC are banished. Thirdly, PEGylation technology is used to modify the surface of the said Fab antibodies to reduce the possibility phagocytosed by reticuloendothelial system so that their detention time in blood circulation system is dramatically extended. This helps to accomplish the goal of sustained release of the said Fab molecules. This solves the problem of half-life shortage in vivo of small Fab molecule so that it is more suitable to be used in vivo while its biological activity is sustained. Compared with the existing monoclonal antibody medicines, the molecules described in this invention are able to extend dramatically dosing intervals. This will further lighten not only a patient's economic burden, but his/her pain caused by injection and manpower loss.

DETAILED DESCRIPTION OF THE EMBODIMENTS

Figure 1:
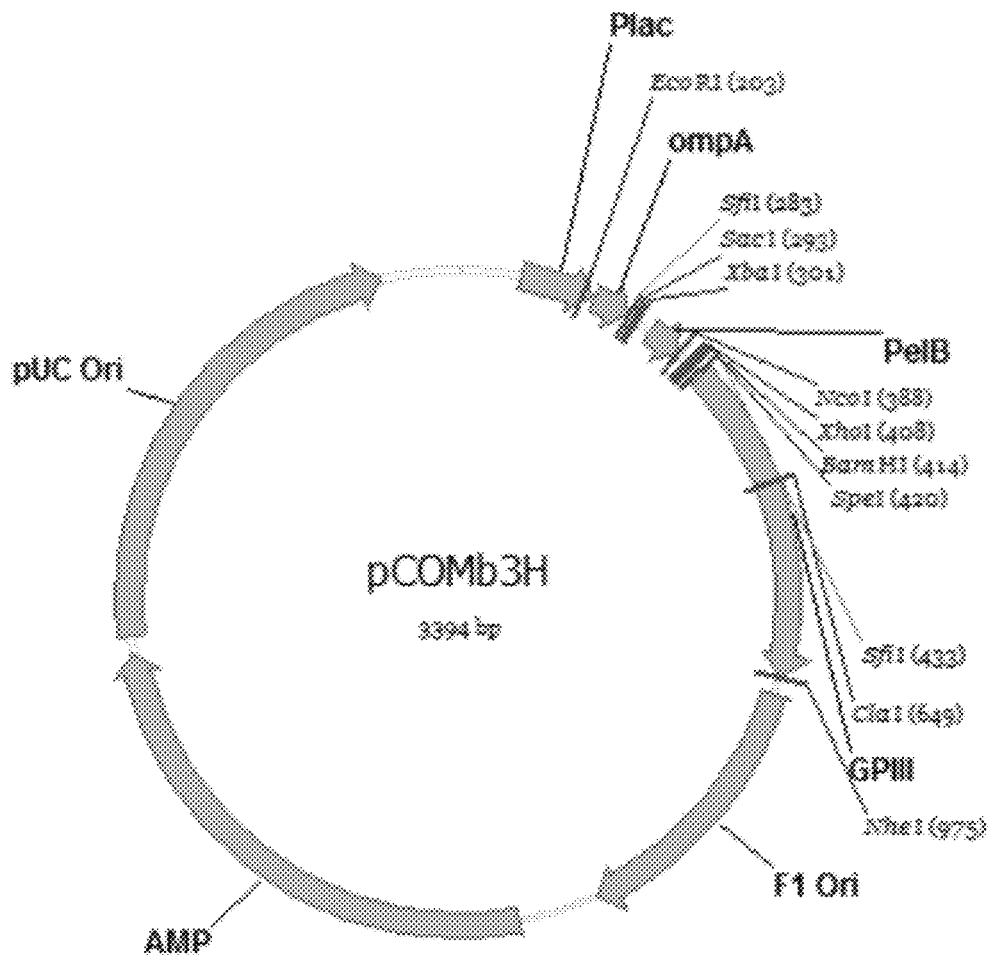
FIG. 1 shows the plasmid structure diagram of the pCOMb3H

Embodiments of the present invention introduced the following experimental strategy:

1. Isolation of Human B Cells Secreting Anti Human TNFα Antibodies:

Leukocytes are isolated from peripheral blood of RA patients using Lymphocyte Isolation Solution and then the positive cells are identified by ELISA after cultured.

2. Isolation of mRNA Coding for Antibodies Specific to Human TNFα

Total RNA is isolated from the above said positive leukocytes and then cDNA is synthesized by the aid of reverse transcription. Then amplify the coding sequences of variable regions of the heavy and light chains of the antibodies to human TNFα by PCR according to SE. Dohmen's method (Journal of Immunological Methods 298 (2005) 9-20, Production of recombinant Ig molecules from antigen-selected single B cells and restricted usage of Ig-gene segments by anti-D antibodies), clone and sequence the obtained coding sequences of the variable regions of both heavy and light chains, and the deduced amino acid sequences of them can be obtained from the sequencing results.

1. The full length coding sequences for both heavy and light chains are identified, and inserted into the expression carrier pcDNA3.1(+)(from Invitrogen). The expression carrier is then used to co-transfect CHO cells to express anti human TNFα antibodies. MTX selection is carried out to increase antibody expression level.

1. The antagonistic function of anti human TNFα antibodies, Fab and Fab-PEG molecules is studied, and compared with that of the existing anti human TNFα antibody, Humira.

The invention would be further described with reference to the following examples, which do not limit the scope of the invention described in the claims. Experimental methods and reagents not described in detail in the following examples can be carried out or prepared based on conventional conditions as described in Sambrook et al, Molecular Cloning, New York: Cold Spring Harbor Laboratory Press, 1989, or manufacturer's manuals.

Example 1

Isolation of Leukocytes Secreting Anti Human TNFα Antibodies 5 ml peripheral blood from an active RA patient is used to isolate leukocytes by the aid of Lymphocyte Isolation Solution, and positive clones are identified based on ELISA assay after the isolated cells cultured.

1. Blood Samples and Primary Screening for TNFα-Binding Positives

In order to isolate human B cells secreting anti human TNFα antibodies, recombinant human TNFα (from Shanghai Sino Biotechnology Co.) is used to coat 96-well plates, 250 ng each well, kept over night before blocking for 2 hours at room temperature with 5% defatted milk dissolved in PBS at pH7.2, washed once with PBS, incubated for 1 hour at Room Temperature (RT), 100 μl serum from different patients be added in each well respectively. Then, the plates are kept for one hour at RT after peroxidase-labeled goat anti-human IgG conjugate is added. After at least 5 washes, TMD or other equivalent chromogenic reagents are added and kept for 20 minutes at RT or 37° C. Stop solution is added. The reaction should keep for at least 10 minutes after adding the chromogenic reagent before 50 µl 1N sulphuric acid solution is added to stop the reactions. Then read the optical absorbance at 450 nm. The positive blood samples with high OD value are selected as candidates.

2. Isolation of Leukocytes from Positive Peripheral Blood Samples

10× Red Cell Lysing Solution is prepared according to the following recipe and procedure:

80 g $NH_4Cl$, 10 g $KHCO_3$ and 3.7 g $Na_4EDTA$ are dissolved in 800 ml $ddH_2O$, adjust the pH to 7.2~7.4 by dropping 1N HCl or 1N NaOH, and add $ddH_2O$ to the final volume of 1000 ml. Then, leukocytes are isolated from the blood samples according to the following procedure.

(1) Anti-coagulated blood samples are spinned at 400-500×g for 5 minutes, aspirate supernatant completely.
(2) 1× Red Cell Lysing Solution is added to the tubes by 6 to 10 volumes of the cell pellet. The pellet is resuspended by repeatedly gentle pipette, and lysing kept for 2 minutes. For example, if the pellet volume is 1 ml, 6 to 10 ml Red Cell Lysing Solution should be added. This step can be carried out at RT or 4° C. Please note: Lysing for 1 to 2 minutes should be enough for mouse blood, but it should be 4 to 5 minutes for human blood. More preferably, the tube is shaken or tapped occasionally to accelerate lysing.
(3) Spinning is done at 400~500×g for 5 minutes, the supernatant is decanted completely. Spinning done at 4□ could be better.
(4) If lysing is found incomplete, the above lysing step could be repeated once or twice. Generally, trace amount red cell leftover would not affect the subsequent procedure.
(5) Washing for 1 or 2 times: appropriate PBS, HBSS, Physiological Saline or medium without serum is added to resuspend the pellet. Spin at 400~500×g for 2-3 minutes, the supernatant is decanted completely. This washing step can be repeated once, twice in total. Generally, the amount of washing buffer in each wash should be at least 5 times of the volume of the pellet. The obtained pellet after spinning at 4° C. is purified leukocytes. TriZol is added to the cell pellet to isolate total RNA according to manufacturer's manual, or stored at −80° C. for later use.

1. mRNA Isolation
(1) TriZol (from Invitrogen, Cat. No. 12183-555) is used to isolate total RNA according to manufacturer's manual, the obtained total RNA samples are stored at −80° C. for later use.
(2) Dynabeads® mRNA Purification Kit (from Invitrogen, Cat. no. 610.06) is used to purify mRNA according to manufacturer's manual, the obtained mRNA samples are used to synthesis cDNA immediately, or stored at −80° C. for later use.

Example 2

Preparation of Anti Human TNFα Antibody Genes

The obtained mRNA samples from different positive blood samples as described above are used as templates, oligo-dT25 (from Shanghai GeneRay biotech. Co.) as primer. The first cDNA chain of the anti TNFα antibody genes are synthesized by MMLV reverse transcriptase (from Invitrogen, Cat. No. 28025-013) according to manufacturer's manual. The obtained first cDNA chain is used as template in the following PCR for amplifying double strained cDNA molecules. In this PCR reaction, Pfu DNA polymerase (from CloneTech) is used to eliminate possible mutations. The primers for heavy and light chains are set forth in the following:

GACATCGAGCTGACCCAGTC    (SEQ ID NO: 1)

Down-Stream Primer for Light Chains:

CTAACACTCTCCCCTGTTGAAGC    (SEQ ID NO: 2)

Up-Stream Primer for Heavy Chains:

GAGGTGCAGCTGGTGGAGTC    (SEQ ID NO: 3)

Down-Stream Primer for Heavy Chains:

CTAGCATGTGTGAGTTTTGTCACAAG    (SEQ ID NO: 4)

PCR Conditions
c) Components of PCR Reaction

| Components | Amount |
| --- | --- |
| 10× PCR Reaction Buffer | 5 µl |
| 25 mM $Mg_2SO_4$ | 5 µl |
| Pfu DNA polymerase (5 U/µl) | 1 µl |
| Up and down primers (2 ug/µl) | 1 µl each, 2 µl in total |
| cDNA | 1.5 µl |
| Triple distilled $H_2O$ | to 50 µl | d) Cycling Conditions:
Predenature: 94° C. 2 minutes
Cycling: 94° C. 1 min, 55° C. 1 min, 72° C. 3 minutes, 20 cycles;
Post extension: 72° C. 5 minutes.
Cycling was carried out in a K960 Thermocycler.
c) Electrophoresis and DNA Recovery from the Gel The products obtained from the above PCR reactions are applied to 1% agarose gel electrophoresis to separate the bands. The obtained bands for light and heavy chains are at about 650 bp and 670 bp in length, which are consistent with their theoretic. The target DNA is extracted from the gel by the aid of Wizard SV Gel and PCR Clean-Up System from Promega according to manufacturer's manual, and 20 µg DNA obtained for each chain.

Construction of Antibody Library and Panning for Anti-Human TNFα Antibodies

Construction of Antibody Library

The above PCR preparations are used to construct Fab antibody library with the vector pCOMb3H that is a derivative of pCOM3 suitable to express Fab molecule. Its full sequence data could be obtained from GenBank (Accession No. AF268280). FIG. 1 is a sketch map illustrating its structure.

The procedure for fully human antibody library construction is revealed and discussed in detail in many publications, and the following are relevant to the same:

1. Dantas, B C, et al., 2005, Construction of a human Fab phage display library from antibody repertoires of osteosarcoma patients. Genet. Mol. Res. 4 (2): 126-140.

2. Hiroshi, T., et al., 1999, Preparation of Recombinant Human Monoclonal Antibody Fab Fragments Specific for *Entamoeba histolytica*, CLINICAL AND DIAGNOSTIC Labor. Immunol, May 1999, 383-387
3. Wu, B P., et al., 2001, Construction and selection of the natural immune Fab antibody phage display library from patients with colorectal cancer, World J Gastroenterol 7(6): 811-815.
4. Lee, C V., et al., 2004, High-affinity Human Antibodies from Phage-displayed Synthetic Fab Libraries with a Single Framework Scaffold, J. Mol. Biol. 340, 1073-1093.
5. Michael H., et al., 2005, Antibody phage display, Mod. Asp. Immunobiol. 15: 47-49.
6. De Haard H J, et al., 1999, A large non-immunized human Fab fragment phage library that permits rapid isolation and kinetic analysis of high affinity antibodies. J Biol Chem 1999, 274:18218-18230.
7. Marks et al. By-passing immunization: human antibodies from V-gene libraries displayed on phage. J. Mol. Biol., 222, 581-597
8. Hoogenboom and Winter, By-passing immunisation: human antibodies from synthetic repertoires of germline VH gene segments rearranged in vitro. J. Mol. Biol., 227, 381-388
9. Haidaris C G Malone J, Sherrill L A, Bliss J M, Gaspari A A, Insel R A, Sullivan M A., Recombinant human antibody single chain variable fragments reactive with *Candida albicans* surface antigens. J Immunol Methods. 2001, 257 (1-2):185-202.
10. Griffiths, A. D., Williams, S. C., Hartley, O., Tomlinson, I. M., Waterhouse, P., Crosby, W. L., Kontermann, R. E., Jones, P. T., Low, N. M., Allison, T. J., Prospero, T. D., Hoogenboom, H. R., Nissim, A., Cox, J. P. L., Harrison, J. L., Zaccolo, M., Gherardi, E. & Winter, G (1994). Isolation of high affinity human antibodies directly from large synthetic repertoires. EMBO J., 13, 3245-3260.
11. Nissim, A., Hoogenboom, H. R., Tomlinson, I. M., Flynn, G, Midgley, C., Lane, D. & Winter, G (1994). Antibody fragments from a 'single pot' phage display library as immunochemical reagents. EMBO J., 13, 692-698.

Panning Procedure

Recombinant human TNFα is used as antigen to pan the above antibody library for Fab molecules with high affinity, the detailed procedure is described as follows.
1. 1 ml resuscitated bacteria harboring the antibody library plasmids is added into 14 ml fresh LB medium in a 50 ml triangle flask, incubated with vigorous shaking for 16 hours at 37° C.
2. The supernatant is transferred to a sterilized 50 ml centrifuge tube after spinning at 12000 RPM for 10 minutes, stored for later use. The titer should be not less than $2 \times 10^{11}$.
3. A 25-ml cell culture bottle is coated with purified recombinant human TNFα by conventional method.
4. Not less than $3 \times 10^{1o}$ phage particles are added in a coated cell culture bottle, incubated for 1 hour at 37° C.
5. The liquid is completely decanted from the bottle, and the bottle is washed 10 times with 10 ml PBS containing 1% Tween-20 each time.
6. 1 ml *E. coli* bacterial strain TG1 cells at log phase are added, and incubated at 37° C. with vigorous shaking for 16 hours.
7. The steps from 2 to 6 are repeated four times.
8. The above cell suspensions are diluted to 100000 cells/ml, then, spreaded onto 1.5% agar plates that contain 0.1% ampicillin.
9. The colonies from the plate are inoculated into wells of 96 deep-well plates, a single colony each well. 960 colonies should be inoculated in ten 96 deep-well plates.
10. The above plates are spinned for 20 minutes at 5000 RPM, then the supernatant is transferred to new 96 deep well plates, and stored at 4° C. for later use.
11. Ten new 96-well plates are coated with 10 μl recombinant human TNFα (10 ug/ml) in each well, then the stored supernatants are added individually with 10 μl each well, and incubated for 1 hour at 37° C., then 20 washes with PBS containing 1% Tween-20 are carried out.
12. 1 μl HRP-labeled goat anti M13 monoclonal antibody is added and mixed well, incubated at 37° C. for 30 minutes before 10 washes with PBS containing 1% Tween-20 are carried out.
13. 200 μl PBS containing 0.025% DAB and 1 μl 1% $H_2O_2$ is added and incubated for 20 minutes to develop the color reaction before reading the data at 595 nm.
14. Wells with high readings are identified after analysis. These clones correspond to variable fragments with high affinities.

486 positive clones are identified from the above said antibody library, and 4 clones with the highest readings are selected, and their affinities are tested.

Affinity assay is carried out according to Scatchard method (Munson et al, 1980, Anal. BioChem., 107:220). The results show that affinities of 4B3, 5F8, 5G4 and 7E2 are as high as $5.17 \times 10^{-7}$, $5.21 \times 10^{-8}$, $7.16 \times 10^{-8}$ 和 $5.43 \times 10^{-6}$.

Molecular Evolution

It is shown in the above results that the affinities of the above clones 5F8 and 5G4 are as high as nanomolar level. For further improvement of their affinities, a sub-library harboring saturated random mutations at CDR3 (ndegapydh) of the 5F8 heavy chain is constructed according to conventional mutation method. From four cycles of panning, in which Humira Fab is used as positive control, 876 positive clones are panned out, and six of them have an affinity better than $10^{-10}$ level, the clones include 7B4, 2H7, 4D3, 6F5, 3C9 and 3H6. Among these, 7B4 and 2H7 have affinities as high as $10^{-12}$ level, equal or even higher than that of Humira Fab. Neutralization ability of these six clones will be assayed in the subsequent experiments.

Example 3

Studies on the Neutralization Ability of the Fab Molecules Specific to Human TNFα

The neutralization abilities of the Fab proteins purified from the above clones were assayed according to the following procedure.
1. L929 cells are cultured to log phase, then digested with Trypsin to separate the cells before diluted to $2 \times 10^5$ cells/ml with cell culture medium.
2. 100 μl of the above cell suspensions are transferred to each well of four 96-well plates, incubated in 5% $CO_2$ for 24 hours at 37° C. in a $CO_2$ incubator.
3. The Fab samples to be measured are diluted with medium containing 1~2 mg/ml Actinomycin D and 0.001 ug/ml TNFα reference material (from Shanghai Sino Biotechnology Co.) to the final concentrations of 10 mg/ml, 1.0 mg/ml, 0.1 mg/ml, 0.01 mg/ml, 0.001 mg/ml, 0.0001 mg/ml and 0.00001 mg/ml. The medium containing 1-2 mg/ml Actinomycin D is used as the negative control and the medium with high dosage of TNFα (2 mg/m) as the positive control.

Figure 3:
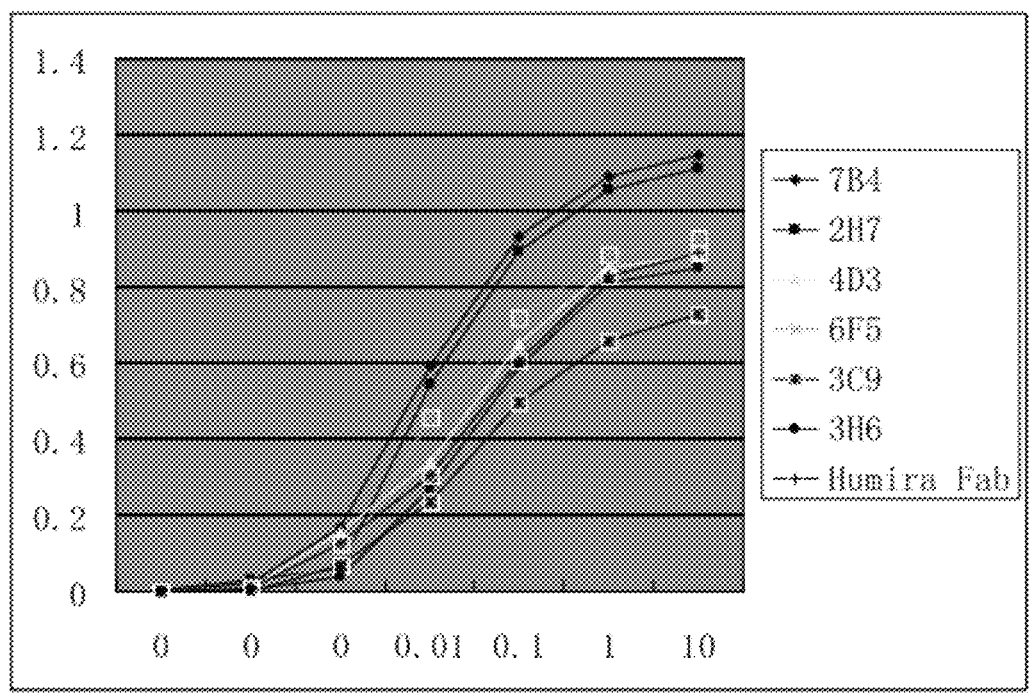
FIG. 3 shows affinity experiment results of 6 Fab clones including 7B4, 2H7, 4D3, 6F5, 3C9 and 3H6.

4. Triplicates (100 μl each well) of the diluted samples at different concentrations, positive and negative controls are aliquoted into a 96-Well plate.
5. The plate is incubated in 5% CO$_2$ for 24 hours at 37° C. or longer. The culturing time should be determined according to the time that all cells in positive control wells get dead.
6. The plates are read to obtain the optical density data after MTT reaction, then a data-based sketch is drawn (see FIG. 3).

It is shown in the data that neutralization abilities of the clones 7B4 and 2H7 are obviously higher than that of Humira-Fab, and other clones are roughly equal to or a little bit lower than that of Humira Fab format.

Example 4

Preparation of Full Length Anti Human TNFα Antibodies

1. DNA Sequencing of Fab Clones 7B4 and 2H7

The Fab clones 7B4 and 2H7 are sequenced by DNA sequencing kit from MBI according to manufacturer's manual. The results indicated that these two clones comprise DNA sequences coding heavy and light chains of human IgG1 type Fab. The sequencing results and deduced amino acid sequences are as follows.

```
7B4 and 2H7 Fab light chain
                                    (SEQ ID NO: 5 645 bp)
GAAATTGTGCTCACACAGTCACCAGACTTTCAGTCTGTcACCCCTAAG GAGAAAGTGACCATcACTTGcAGGGCcTCTCAGTTCGTcGGCTATAGT

ATCCACTGGTACCAGCAGAAACCCGATCAGTCCCCTAAACTGCTGATC

AAGTACGCcTCTGAATCAAGGTCAGGTGTCCCCAGTCGATTTTCTGGA

TCAGGATCTGGTACCGACTTCACCCTCACCATcAATAGCTTGGAGGCC

GAGGACGCtGCTACCTACTACTGCCAACAAAGCCACAGCTGGCACTTT

ACTTTCGGTCAGGGCACCAAGGTcGAGATTAAGCGCACAGTGGCCGCT

CCCTCAGTgTTCATCTTCCCACCTTCAGACGAGCAActgAAGAGCGGC

ACTGCCAGCGTCGTGTGTCTGCTGAACAACTTCTACCCCAGGGAAGCT

AAAGTGCAGTGGAAAGTGGATAATGCTCTGCAATCCGGCAACTCCCAG

GAGTCCGTGACCGAGCAGGATAGTAAGGACTCCACATATAGCCTCTCA

AGCACActcACCTTGAGCAAGGCTGACTACGAGAAGCATAAGGTGTAT

GCCTGTGAAGTGACACATCAGGGGCTCTCCAGTCCTGTGACAAAGTCC

TTCAACCGGGGCGAATGCTAG,

7B4 Fab H chain
                                    (SEQ ID NO: 6 687 bp)
GAAGTCCAGCTGGTCGAGAGCGGTGGCGGGCTGGTGCAACCcGGTGGA TCACTGCGGCTCAGCTGCGCTGCTAGTGGcTTTcccTTCTCTAACCAC

TGGATGAATTGGGTCCGGCAGGCTCCAGGAAAGGGTCTGGAGTGGGTG

GGTGAGATCAGgAGTAAGTCTATGAACTCCGCCACACACTATGCTGAA

AGCGTGAAAGGGCGCTTCACAATCTCTAGAGACGATTCAAAGAACTCT

CTGTACCTGCAGATGAAcAGTCTGAAAACAGAGGACACCGCTGTGTAT

TACTGTGCTCGGaacgactacggtgcagcttacgaccacTGGGGCCAA

GGTACACTGGTCACCGTCTCGAGTGCCTCCACCAAGGGCCCATCGGTC

TTCCCCCTGGCACCCTCCTCCAAGAGCACCTCTGGGGGCACAGCGGCC

CTGGGCTGCCTGGTCAAGGACTACTTCCCCGAACCGGTGACGGTGTCG

TGGAACTCAGGCGCCCTGACCAGCGGCGTGCACACCTTCCCGGCTGTC

CTACAGTCCTCAGGACTCTACTCCCTCAGCAGCGTGGTGACCGTGCCC

TCCAGCAGCTTGGGCACCCAGACCTACATCTGCAACGTGAATCACAAG

CCCAGCAACACCAAGGTGGACAAGAGAGTTGAGCCCAAATCTTGTGAC

AAAACTCACACATGC

2H7 Fab H chain
                                    (SEQ ID NO: 7 687 bp)
GAAGTCCAGCTGGTCGAGAGCGGTGGCCGGCTGGTGCAACCCGGTGGA

TCACTGCGGCTCAGCTGCGCTGCTAGTGGCTTTCCCTTCTCTAACCAC

TGGATGAATTGGGTCCGGCAGGCTCCAGGAAAGGGTCTGGAGTGGGTG

GGTGAGATCAGGAGTAAGTCTATGAACTCCGCCACACACTATGCTGAA

AGCGTGAAAGGGCGCTTCACAATCTCTAGAGACGATTCAAAGAACTCT

CTGTACCTGCAGATGAACAGTCTGAAAACAGAGGACACCGCTGTGTAT

TACTGTGCTCGGaacgtcgacggtgcaccttacgaccacTGGGGCCAA

GGTACACTGGTCACCGTCTCGAGTGCCTCCACCAAGGGCCCATCGGTC

TTCCCCCTGGCACCCTCCTCCAAGAGCACCTCTGGGGGCACAGCGGCC

CTGGGCTGCCTGGTCAAGGACTACTTCCCCGAACCGGTGACGGTGTCG

TGGAACTCAGGCGCCCTGACCAGCGGCGTGCACACCTTCCCGGCTGTC

CTACAGTCCTCAGGACTCTACTCCCTCAGCAGCGTGGTGACCGTGCCC

TCCAGCAGCGTGGGCACCCAGACCTACATCTGCAACGTGAATCACAAG

CCCAGCAACACCAAGGTGGACAAGAGAGTTGAGCCCAAATCTTGTGAC

AAAACTCACACATGC
```

Deduced Amino Acid Sequences:

```
7B4 and 2H7 Fab L chain
                                    (SEQ ID NO: 8)
DIQMTQSPSYLSASVGDRVTITCRASQGSVGDRAWYQQKPGKAPKLLI

YAASTLQSGVPSRFSGSGSGTDFTLTISSLQPEPKLLIYKASSLESGV

TFGQGTKLIEIKRTVAAPSVFIFPPSDEQLKSGTASVVCLLNNEYPRE

AKVQWKVDNALQSGNSQESVTEQDSKDSTYSLSSTLTLSKADYEKHKV

YACEVTHQGLSSTPVTKSFNRGEC

7B4 Fab H chain
                                    (SEQ ID NO: 9 229aa)
EVQLVESGGGLVQPGGSLRLSCAASGFPFSNHWMNWVRQAPGKGLEWV

GEIRSKSMNSATHYAESVKGRFTISRDDSKNSLYLQMNSLKTEDTAVY

YCARndygaaydhWGQGTLVTVSSASTKGPSVFPLAPSSKSTSGGTAA

LGCLVKDYFPEPVTVSWNSGALTSGVHTFPAVLQSSGLYSLSSVVTVP

SSSLGTQTYICNVNHKPSNTKVDKRVEPKSCDKTHTC

2H7 Fab H chain
                                    (SEQ ID NO: 10 229aa)
EVQLVESGGRLVQPGGSLRLSCAASGFPFSNHWMNWVRQAPGKGLEWV

GEIRSKSMNSATHYAESVKGRFTISRDDSKNSLYLQMNSLKTEDTAVY

YCARnvdgapydhWGQGTLVTVSSASTKGPSVFPLAPSSKSTSGGTAA
```

LGCLVKDYFPEPVTVSWNSGALTSGVHTFPAVLQSSGLYSLSSVVTVP

SSSVGTQTYICNVNHKPSNTKVDKRVEPKSCDKTHTC

1. Acquirement of Fc Fragment of Human IgG1 Heavy Chain

In order to express full length antibody, DNA fragments coding heavy chain signal peptide (MEFGLSWLFLVAILKGVQC) (residues 1-19 of SEQ ID NO: 16) and Fc fragment of human IgG1 are synthesized to construct full length anti human TNFα antibody genes. Based on publications, the DNA sequence coding for the signal peptide and Fc fragment of human IgG1 heavy chain are:

```
Coding sequence of signal peptide of human IgG1
heavy chain (5'→3')
                                        (SEQ ID NO: 11)
ATGGAGTTCGGACTCAGTTGGCTGTTCCTGGTGGCCATCCTGAAGGGT

GTGCAGTGT

Coding sequence of Fc fragment of human IgG1
heavy chain (5'→3')
                                        (SEQ ID NO: 12)
ACATGCCCACCGTGCCCAGCACCTGAACTCCTGGGGGGACCGTCAGTC

TTCCTCTTCCCCCCAAAACCCAAGGACACCCTCATGATCTCCCGGACC

CCTGAGGTCACATGCGTGGTGGTGGACGTGAGCCACGAAGACCCTGAG

GTCAAGTTCAACTGGTACGTGGACGGCGTGGAGGTGCATAATGCCAAG

ACAAAGCCGCGGGAGGAGCAGTACAACAGCACGTACCGTGTGGTCAGC

GTCCTCACCGTCCTGCACCAGGACTGGCTGAATGGCAAGGAGTACAAG

TGCAAGGTCTCCAACAAAGCCCTCCCAGCCCCCATCGAGAAAACCATC

TCCAAAGCCAAAGGGCAGCCCCGAGAACCACAGGTGTACACCCTGCCC

CCATCCCGGGATGAGCTGACCAAGAACCAGGTCAGCCTGACCTGCCTG

GTCAAAGGCTTCTATCCCAGCGACATCGCCGTGGAGTGGGAGAGCAAT

GGGCAGCCGGAGAACAACTACAAGACCACGCCTCCCGTGCTGGACTCC

GACGGCCCCTTCTTCCTCTACAGCAAGCTCACCGTGGACAAGAGCAGG

TGGCAGCAGGGGAACGTCTTCTCATGCTCCGTGATGCATGAGGCTCTG

CACAACCACTACACGCAGAAGAGCCTCTCCCTGTCTCCGGGTAAA
```

The above DNA sequences were synthesized by the aid of conventional PCR-based DNA synthesis method.

A signal peptide (MDMRVPAQLLGLLLLWLRGARC, SEQ ID NO:13) coding sequence (ATGGACATGCGGGTTCCAGCCCAGCTTCTCGGACTTCTGCTgTTGTGGCTGCGCGGAGC ACGGTGc, SEQ ID NO:14) for the Fab light chain was synthesized and added to Fab light chain to form a full length light chain DNA molecule.

2. Production of Expressed Full Length Anti Human TNFα Monoclonal Antibody

The synthesized Fc coding fragment coding region for heavy chain variable region and signal peptide as above are integrated together by conventional overlapping PCR procedure to form full length heavy chain. During this procedure, a SalI site and an XbaI site are added to the 5'- and 3'-ends, respectively, and two protection bases are added to each end. The integrated full length heavy chain comprises 1428 bp. This fragment is the coding region of full length heavy chain, and the DNA sequences coding full length heavy chain for 7B4 and 2H7 are listed as follows (SEQ ID NO: 15, SEQ ID NO: 16, SEQ ID NO:17, SEQ ID NO:18).

```
                                        SEQ ID NO: 15
gagtcgacATGGAGTTCGGACTCAGTTGGCTGTTCCTGGTGGCCATCC

TGAAGGGTGTGCAGTGTGAAGTCCAGCTGGTCGAGAGCGGTGGCGGGC

TGGTGCAACCcGGTGGATCACTGCGGCTCAGCTGCGCTGCTAGTGGcT

TTCCCTTCTCTAACCACTGGATGAATTGGGTCCGGCAGGCTCCAGGAA

AGGGTCTGGAGTGGGTGGGTGAGATCAGgAGTAAGTCTATGAACTCCG

CCACACACTATGCTGAAAGCGTGAAAGGGCGCTTCACAATCTCTAGAG

ACGATTCAAAGAACTCTCTGTACCTGCAGATGAAcAGTCTGAAAACAG

AGGACACCGCTGTGTATTACTGTGCTCGGaacgactacggtgcagctt acgaccacTGGGGCCAAGGTACACTGGTCACCGTCTCGAGTGCCTCCA

CCAAGGGCCCATCGGTCTTCCCCCTGGCACCCTCCTCCAAGAGCACCT

CTGGGGGCACAGCGGCCCTGGGCTGCCTGGTCAAGGACTACTTCCCCG

AACCGGTGACGGTGTCGTGGAACTCAGGCGCCCTGACCAGCGGCGTGC

ACACCTTCCCGGCTGTCCTACAGTCCTCAGGACTCTACTCCCTCAGCA

GCGTGGTGACCGTGCCCTCCAGCAGCTTGGGCACCCAGACCTACATCT

GCAACGTGAATCACAAGCCCAGCAACACCAAGGTGGACAAGAGAGTTG

AGCCCAAATCTTGTGACAAAACTCACACATGCACATGCCCACCGTGCC

CAGCACCTGAACTCCTGGGGGGACCGTCAGTCTTCCTCTTCCCCCCAA

AACCCAAGGACACCCTCATGATCTCCCGGACCCCTGAGGTCACATGCG

TGGTGGTGGACGTGAGCCACGAAGACCCTGAGGTCAAGTTCAACTGGT

ACGTGGACGGCGTGGAGGTGCATAATGCCAAGACAAAGCCGCGGGAGG

AGCAGTACAACAGCACGTACCGTGTGGTCAGCGTCCTCACCGTCCTGC

ACCAGGACTGGCTGAATGGCAAGGAGTACAAGTGCAAGGTCTCCAACA

AAGCCCTCCCAGCCCCCATCGAGAAAACCATCTCCAAAGCCAAAGGGC

AGCCCCGAGAACCACAGGTGTACACCCTGCCCCCATCCCGGGATGAGC

TGACCAAGAACCAGGTCAGCCTGACCTGCCTGGTCAAAGGCTTCTATC

CCAGCGACATCGCCGTGGAGTGGGAGAGCAATGGGCAGCCGGAGAACA

ACTACAAGACCACGCCTCCCGTGCTGGACTCCGACGGCCCCTTCTTCC

TCTACAGCAAGCTCACCGTGGACAAGAGCAGGTGGCAGCAGGGGAACG

TCTTCTCATGCTCCGTGATGCATGAGGCTCTGCACAACCACTACACGC

AGAAGAGCCTCTCCCTGTCTCCGGGTAAATAGtctagagc(1432 bp)
```

The Deduced Amino Acid Sequences are:

```
                                          Seq ID NO: 16
MEFGLSWLFLVAILKGVQCEVQLVESGGGLVQPGGSLRLSCAASGFPF

SNHWMNWVRQAPGKGLEWVGEIRSKSMNSATHYAESVKGRFTISRDDS

KNSLYLQMNSLKTEDTAVYYCARNDYGAAYDHWGQGTLVTVSSASTKG

PSVFPLAPSSKSTSGGTAALGCLVKDYFPEPVTVSWNSGALTSGVHTF

PAVLQSSGLYSLSSVVTVPSSSLGTQTYICNVNHKPSNTKVDKRVEPK

SCDKTHTCTCPPCPAPELLGGPSVFLFPPKPKDTLMISRTPEVTCVVV

DVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTK
```

-continued
NQVSLTCLVKGFYPSDIAVEWESNGQPENNYKTTPPVLDSDGPFFLYS

KLTVDKSRWQQGNVFSCSVMHEALHNHYTQKSLSLSPGK.

Seq ID NO: 17
gagtcgacATGGAGTTCGGACTCAGTTGGCTGTTCCTGGTGGCCATCC

TGAAGGGTGTGCAGTGT<u>GAAGTCCAGCTGGTCGAGAGCGGTGGCGGGC</u>

<u>TGGTGCAACCcGGTGGATCACTGCGGCTCAGCTGCGCTGCTAGTGGcT</u>

<u>TTCCCTTCTCTAACCACTGGATGAATTGGGTCCGGCAGGCTCCAGGAA</u>

<u>AGGGTCTGGAGTGGGTGGGTGAGATCAGgAGTAAGTCTATGAACTCCG</u>

<u>CCACACACTATGCTGAAAGCGTGAAAGGGCGCTTCACAATCTCTAGAG</u>

<u>ACGATTCAAAGAACTCTCTGTACCTGCAGATGAAcAGTCTGAAAACAG</u>

<u>AGGACACCGCTGTGTATTACTGTGCTCGG</u>aacgtcgacggtgcacctt acgaccac<u>TGGGGCCAAGGTACACTGGTCACCGTCTCGAGTGCCTCCA</u>

<u>CCAAGGGCCCATCGGTCTTCCCCCTGGCACCCTCCTCCAAGAGCACCT</u>

<u>CTGGGGGCACAGCGGCCCTGGGCTGCCTGGTCAAGGACTACTTCCCCG</u>

<u>AACCGGTGACGGTGTCGTGGAACTCAGGCGCCCTGACCAGCGGCGTGC</u>

<u>ACACCTTCCCGGCTGTCCTACAGTCCTCAGGACTCTACTCCCTCAGCA</u>

<u>GCGTGGTGACCGTGCCCTCCAGCAGCTTGGGCACCCAGACCTACATCT</u>

<u>GCAACGTGAATCACAAGCCCAGCAACACCAAGGTGGACAAGAGAGTTG</u>

<u>AGCCCAAATCTTGTGACAAAACTCACACATGCACATGCCCACCGTGCC</u>

<u>CAGCACCTGAACTCCTGGGGGACCGTCAGTCTTCCTCTTCCCCCCAA</u>

<u>AACCCAAGGACACCCTCATGATCTCCCGGACCCCTGAGGTCACATGCG</u>

<u>TGGTGGTGGACGTGAGCCACGAAGACCCTGAGGTCAAGTTCAACTGGT</u>

<u>ACGTGGACGGCGTGGAGGTGCATAATGCCAAGACAAAGCCGCGGGAGG</u>

<u>AGCAGTACAACAGCACGTACCGTGTGGTCAGCGTCCTCACCGTCCTGC</u>

<u>ACCAGGACTGGCTGAATGGCAAGGAGTACAAGTGCAAGGTCTCCAACA</u>

<u>AAGCCCTCCCAGCCCCCATCGAGAAAACCATCTCCAAAGCCAAAGGGC</u>

<u>AGCCCCGAGAACCACAGGTGTACACCCTGCCCCCATCCCGGGATGAGC</u>

<u>TGACCAAGAACCAGGTCAGCCTGACCTGCCTGGTCAAAGGCTTCTATC</u>

<u>CCAGCGACATCGCCGTGGAGTGGGAGAGCAATGGGCAGCCGGAGAACA</u>

<u>ACTACAAGACCACGCCTCCCGTGCTGGACTCCGACGGCCCCTTCTTCC</u>

<u>TCTACAGCAAGCTCACCGTGGACAAGAGCAGGTGGCAGCAGGGGAACG</u>

<u>TCTTCTCATGCTCCGTGATGCATGAGGCTCTGCACAACCACTACACGC</u>

<u>AGAAGAGCCTCTCCCTGTCTCCGGGTAAATAG</u>tctagagc(1432 bp)

The Deduced Amino Acid Sequences are:

SEQ ID NO: 18
MEFGLSWLFLVAILKGVQCEVQLVESGGGLVQPGGSLRLSCAASGFPF

SNHWMNWVRQAPGKGLEWVGEIRSKSMNSATHYAESVKGRFTISRDDS

KNSLYLQMNSLKTEDTAVYYCARNVDGAPYDHWGQGTLVTVSSASTKG

PSVFPLAPSSKSTSGGTAALGCLVKDYFPEPVTVSWNSGALTSGVHTF

PAVLQSSGLYSLSSVVTVPSSSLGTQTYICNVNHKPSNTKVDKRVEPK

-continued
SCDKTHTCTCPPCPAPELLGGPSVFLFPPKPKDTLMISRTPEVTCVVV

DVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTK

NQVSLTCLVKGFYPSDIAVEWESNGQPENNYKTTPPVLDSDGPFFLYS

KLTVDKSRWQQGNVFSCSVMHEALHNHYTQKSLSLSPGK.

The same methods are applied to synthesize and add the coding region ATGGACATGCGGGTTCCAGCCCAGCTTCTCGGACTTCTGCTGTTGTGGCTGCGCGGAGCACGGTGC (SEQ ID NO: 14) of signal peptide (MDMRVPAQLLGLLLLWLRGARC) (SEQ ID NO: 13) to light chain Fab, and add NheI, EcoRI sites and protection bases to 5'- and 3'-ends to form the full length DNA molecule of light chain (SEQ ID NO: 19).

(SEQ ID NO: 19)
ctgctagcATGGACATGCGGGTTCCAGCCCAGCTTCTCGGACTTCTGC

TgTTGTGGCTGCGCGGAGCACGGTGcGAAATTGTGCTCACACAGTCAC

CAGACTTTCAGTCTGTCACCCCTAAGGAGAAAGTGACCATCACTTGCA

GGGCCTCTCAGTTCGTCGGCTATAGTATCCACTGGTACCAGCAGAAAC

CCGATCAGTCCCCTAAACTGCTGATCAAGTACGCCTCTGAATCAAGGT

CAGGTGTCCCCAGTCGATTTTCTGGATCAGGATCTGGTACCGACTTCA

CCCTCACCATCAATAGCTTGGAGGCCGAGGACGCTGCTACCTACTACT

GCCAACAAAGCCACAGCTGGCACTTTACTTTCGGTCAGGGCACCAAGG

TCGAGATTAAGCGCACAGTGGCCGCTCCCTCAGTGTTCATCTTCCCAC

CTTCAGACGAGCAACTGAAGAGCGGCACTGCCAGCGTCGTGTGTCTGC

TGAACAACTTCTACCCCAGGGAAGCTAAAGTGCAGTGGAAAGTGGATA

ATGCTCTGCAATCCGGCAACTCCCAGGAGTCCGTGACCGAGCAGGATA

GTAAGGACTCCACATATAGCCTCTCAAGCACACTCACCTTGAGCAAGG

CTGACTACGAGAAGCATAAGGTGTATGCCTGTGAAGTGACACATCAGG

GGCTCTCCAGTCCTGTGACAAAGTCCTTCAACCGGGGCGAATGCTAGg aattctc(723 bp)

Figure 2:
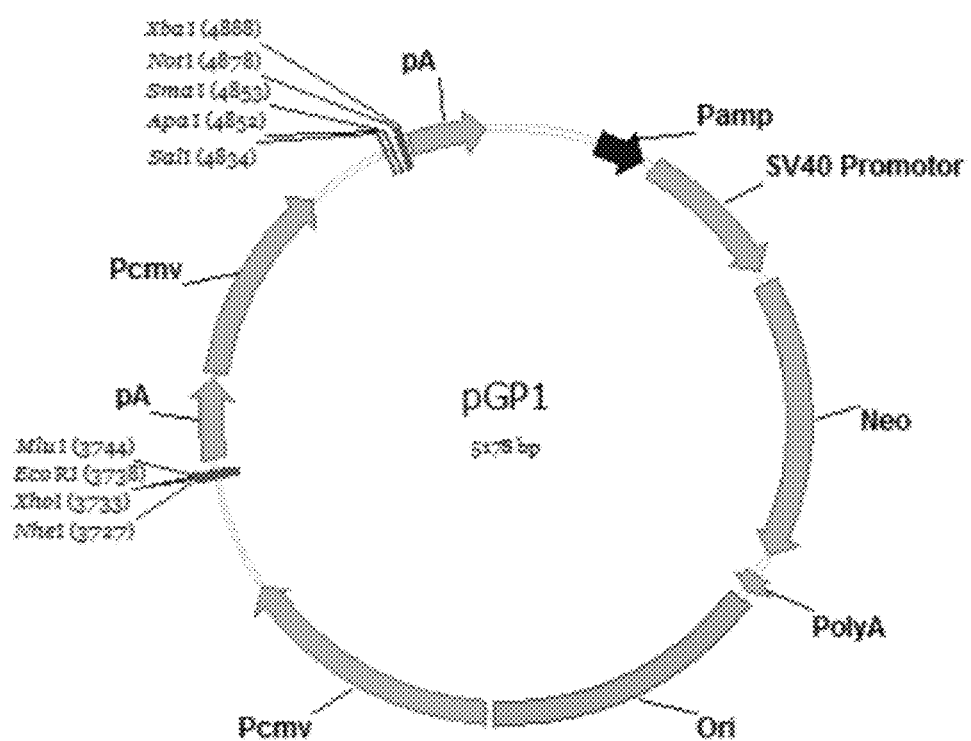
FIG. 2 shows the plasmid structure diagram of the expression vector pGP1

The above full length light chain (SEQ ID NO: 19) is inserted into NheI/EcoRI sites of pGP1 expression vector (FIG. 2), the correct clones verified by sequencing after restriction digestion screening is designated as pGP1L. Then, the above full length heavy chain (SEQ ID NO:15 和 SEQ ID NO:17) is inserted into SalI/XbaI sites of pGP1L, correct clones as verified by sequencing were designated as pGP17B4L 和 pGP12H7L. As revealed by checkup, the expressed products correspond to the theoretical anticipation.

3. Transfection and Selection of CHO Cells

CHO cells are transfected with plasmid DNA of pGP1/7B4L and pGP1/2H7L via conventional method.

In the present invention, LipoFamine 2000 from Invitrogen is used to transfect CHO cells. 100 ug purified DNA samples of the two plasmids bearing both heavy and light chain are used to transfect CHO cells according to manufacturer's manual.

The CHO cells are selected with G418 for three weeks after transfection, and the concentration is started from 0.05 μM and increased to 10 μM, roughly the concentration doubles every two weeks according to cell growth conditions. Cell culture is carried out conventionally with medium comprising RPM1640/DEME plus 15% fetal bovine serum from GIBCO in 5% $CO_2$ at 37° C. in an incubator. Then, the cells are colonized by conventional limited dilution. ELISA method is applied to verify the antibody expression of the obtained recombinant cell lines. The clones with high expression level are selected to express recombinant antibodies.

The expressed antibodies are simply purified with Protein A Sepharose CL-4B (GE, Cat. No.: 17-0963-02) according to manufacturer's manual. The obtained products of the two expression vectors are named respectively as 7B4L and 2H7L. As revealed by checkup, the expressed products are consistent with theoretically anticipated.

Example 5

Studies on the Neutralization Ability of the Full Length Antibodies Specific to Human TNFα

Figure 4:
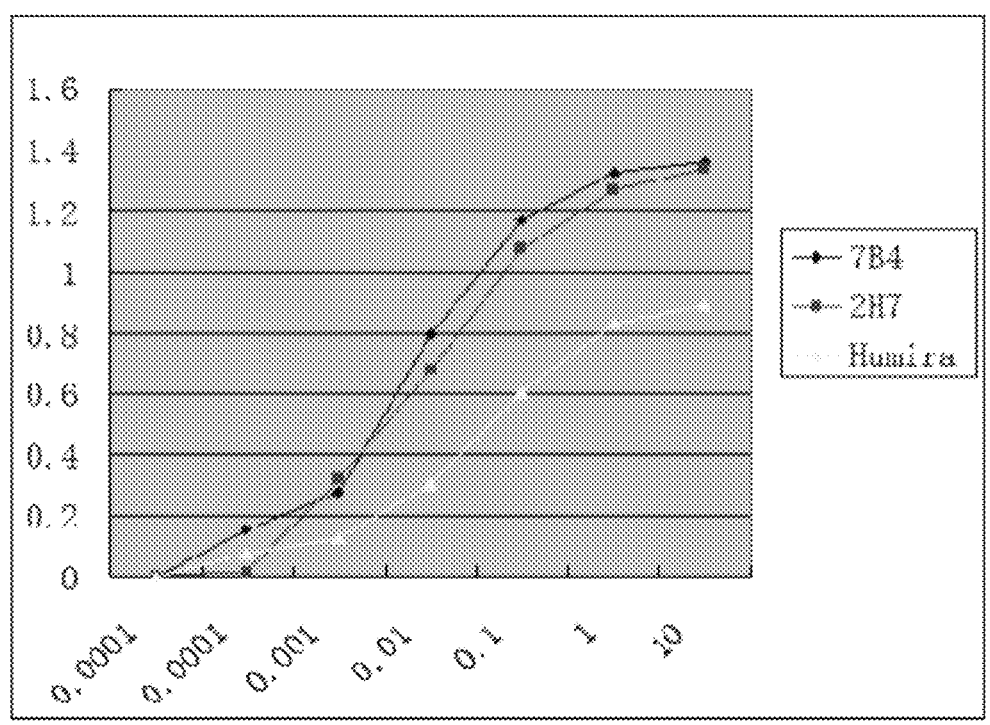
FIG. 4 shows experiment results of the neutralization ability of full length molecules 7B4 and 2H7.

The purified full length anti human TNFα monoclonal antibodies obtained above are tested for their neutralization ability to human TNFα according to the method described in Example 3, positive control is Humira. The results are shown in FIG. 4.

From the obtained data, it can be concluded that the neutralization abilities of the full length 7B4L and 2H7L are increased obviously compared with that of Humira.

What is claimed is:

1. An anti-human TNFα monoclonal antibody, comprising:
   a) a light chain amino acid sequence comprising SEQ ID NO: 8; and
   b) a heavy chain amino acid sequence comprising SEQ ID NO: 9, SEQ ID NO: 10 or SEQ ID NO: 18.

2. The antibody of claim 1, wherein the heavy chain amino acid sequence comprises SEQ ID NO: 16.

3. The Fab format of the anti-TNFα monoclonal antibody of claim 1.

4. A pharmaceutical composition comprising: the antibody of claim 1 wherein said antibody is capable of treating inflammatory diseases relating to TNFα.

5. A pharmaceutical composition comprising: the antibody of claim 2, wherein said antibody is capable of treating inflammatory diseases relating to TNFα.

6. A pharmaceutical composition comprising: the Fab format of claim 3, wherein said Fab format is capable of treating inflammatory diseases relating to TNFα.

* * * * *

```
                        SEQUENCE LISTING

<160> NUMBER OF SEQ ID NOS: 19

<210> SEQ ID NO 1
<211> LENGTH: 20
<212> TYPE: DNA
<213> ORGANISM: artificial sequence
<220> FEATURE:
<223> OTHER INFORMATION: Primer

<400> SEQUENCE: 1
gacatcgagc tgacccagtc                                                  20

<210> SEQ ID NO 2
<211> LENGTH: 23
<212> TYPE: DNA
<213> ORGANISM: artificial sequence
<220> FEATURE:
<223> OTHER INFORMATION: primers

<400> SEQUENCE: 2
ctaacactct cccctgttga agc                                              23

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
gaggtgcagc tggtggagtc                                                  20

<210> SEQ ID NO 4
<211> LENGTH: 26
<212> TYPE: DNA
<213> ORGANISM: artificial sequence
<220> FEATURE:
<223> OTHER INFORMATION: primer

<400> SEQUENCE: 4
ctagcatgtg tgagttttgt cacaag                                           26

<210> SEQ ID NO 5
<211> LENGTH: 645
<212> TYPE: DNA
<213> ORGANISM: artificial sequence
<220> FEATURE:
<223> OTHER INFORMATION: coding gene of light chain Fab region

<400> SEQUENCE: 5
gaaattgtgc tcacacagtc accagacttt cagtctgtca cccctaagga gaaagtgacc      60
```

| | |
|---|---|
| atcacttgca gggcctctca gttcgtcggc tatagtatcc actggtacca gcagaaaccc | 120 |
| gatcagtccc ctaaactgct gatcaagtac gcctctgaat caaggtcagg tgtccccagt | 180 |
| cgattttctg gatcaggatc tggtaccgac ttcacccctca ccatcaatag cttggaggcc | 240 |
| gaggacgctg ctacctacta ctgccaacaa agccacagct ggcactttac tttcggtcag | 300 |
| ggcaccaagg tcgagattaa gcgcacagtg gccgctccct cagtgttcat cttcccacct | 360 |
| tcagacgagc aactgaagag cggcactgcc agcgtcgtgt gtctgctgaa caacttctac | 420 |
| cccagggaag ctaaagtgca gtggaaagtg gataatgctc tgcaatccgg caactcccag | 480 |
| gagtccgtga ccgagcagga tagtaaggac tccacatata gcctctcaag cacactcacc | 540 |
| ttgagcaagg ctgactacga aagcataag gtgtatgcct gtgaagtgac acatcagggg | 600 |
| ctctccagtc ctgtgacaaa gtccttcaac cggggcgaat gctag | 645 |

<210> SEQ ID NO 6
<211> LENGTH: 687
<212> TYPE: DNA
<213> ORGANISM: artificial sequence
<220> FEATURE:
<223> OTHER INFORMATION: coding sequence for 7B4 heavy chain

<400> SEQUENCE: 6

| | |
|---|---|
| gaagtccagc tggtcgagag cggtggcggg ctggtgcaac ccggtggatc actgcggctc | 60 |
| agctgcgctg ctagtggctt tcccttctct aaccactgga tgaattgggt ccggcaggct | 120 |
| ccaggaaagg gtctggagtg ggtgggtgag atcaggagta agtctatgaa ctccgccaca | 180 |
| cactatgctg aaagcgtgaa agggcgcttc acaatctcta gagacgattc aaagaactct | 240 |
| ctgtacctgc agatgaacag tctgaaaaca gaggacaccg ctgtgtatta ctgtgctcgg | 300 |
| aacgactacg gtgcagctta cgaccactgg ggccaaggta cactggtcac cgtctcgagt | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag cgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttgagccc | 660 |
| aaatcttgtg acaaaactca cacatgc | 687 |

<210> SEQ ID NO 7
<211> LENGTH: 687
<212> TYPE: DNA
<213> ORGANISM: artificial sequence
<220> FEATURE:
<223> OTHER INFORMATION: coding sequence for 2H7 heavy chain

<400> SEQUENCE: 7

| | |
|---|---|
| gaagtccagc tggtcgagag cggtggccgg ctggtgcaac ccggtggatc actgcggctc | 60 |
| agctgcgctg ctagtggctt tcccttctct aaccactgga tgaattgggt ccggcaggct | 120 |
| ccaggaaagg gtctggagtg ggtgggtgag atcaggagta agtctatgaa ctccgccaca | 180 |
| cactatgctg aaagcgtgaa agggcgcttc acaatctcta gagacgattc aaagaactct | 240 |
| ctgtacctgc agatgaacag tctgaaaaca gaggacaccg ctgtgtatta ctgtgctcgg | 300 |
| aacgtcgacg gtgcacctta cgaccactgg ggccaaggta cactggtcac cgtctcgagt | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |

```
tggaactcag gcgccctgac cagcggcgtg cacaccttcc cggctgtcct acagtcctca    540
ggactctact ccctcagcag cgtggtgacc gtgccctcca gcagcgtggg cacccagacc    600
tacatctgca acgtgaatca caagcccagc aacaccaagg tggacaagag agttgagccc    660
aaatcttgtg acaaaactca cacatgc                                        687
```

```
<210> SEQ ID NO 8
<211> LENGTH: 216
<212> TYPE: PRT
<213> ORGANISM: artificial sequence
<220> FEATURE:
<223> OTHER INFORMATION: amino acid sequence of Fab light chain

<400> SEQUENCE: 8

Asp Ile Gln Met Thr Gln Ser Pro Ser Tyr Leu Ser Ala Ser Val Gly
1               5                  10                  15

Asp Arg Val Thr Ile Thr Cys Arg Ala Ser Gln Gly Ser Val Gly Asp
            20                  25                  30

Arg Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Pro Lys Leu Leu Ile Tyr Lys Ala Ser Ser Leu Glu Ser Gly Val
                85                  90                  95

Thr Phe Gly Gln Gly Thr Lys Leu Ile Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 9
<211> LENGTH: 229
<212> TYPE: PRT
<213> ORGANISM: artificial sequence
<220> FEATURE:
<223> OTHER INFORMATION: amino acid sequence of 7B4 heavy chain

<400> SEQUENCE: 9

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Pro Phe Ser Asn His
            20                  25                  30

Trp Met Asn Trp Val Arg Gln Ala Pro Gly Lys Gly Leu Glu Trp Val
        35                  40                  45
```

```
Gly Glu Ile Arg Ser Lys Ser Met Asn Ser Ala Thr His Tyr Ala Glu
            50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                    85                  90                  95

Tyr Cys Ala Arg Asn Asp Tyr Gly Ala Ala Tyr Asp His Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
            210                 215                 220

Lys Thr His Thr Cys
225

<210> SEQ ID NO 10
<211> LENGTH: 229
<212> TYPE: PRT
<213> ORGANISM: artificial sequence
<220> FEATURE:
<223> OTHER INFORMATION: amino acid sequence of 2H7 heavy chain

<400> SEQUENCE: 10

Glu Val Gln Leu Val Glu Ser Gly Gly Arg Leu Val Gln Pro Gly Gly
  1               5                  10                  15

Ser Leu Arg Leu Ser Cys Ala Ala Ser Gly Phe Pro Phe Ser Asn His
                20                  25                  30

Trp Met Asn Trp Val Arg Gln Ala Pro Gly Lys Gly Leu Glu Trp Val
                35                  40                  45

Gly Glu Ile Arg Ser Lys Ser Met Asn Ser Ala Thr His Tyr Ala Glu
            50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                    85                  90                  95

Tyr Cys Ala Arg Asn Val Asp Gly Ala Pro Tyr Asp His Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190
Ser Ser Ser Val Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
        210                 215                 220

Lys Thr His Thr Cys
225

<210> SEQ ID NO 11
<211> LENGTH: 57
<212> TYPE: DNA
<213> ORGANISM: Homo sapiens

<400> SEQUENCE: 11
atggagttcg gactcagttg gctgttcctg gtggccatcc tgaagggtgt gcagtgt      57

<210> SEQ ID NO 12
<211> LENGTH: 669
<212> TYPE: DNA
<213> ORGANISM: Homo sapiens

<400> SEQUENCE: 12
acatgcccac cgtgcccagc acctgaactc ctggggggac cgtcagtctt cctcttcccc     60
ccaaaaccca aggacaccct catgatctcc cggacccctg aggtcacatg cgtggtggtg    120
gacgtgagcc acgaagaccc tgaggtcaag ttcaactggt acgtggacgg cgtggaggtg    180
cataatgcca agacaaagcc gcgggaggag cagtacaaca gcacgtaccg tgtggtcagc    240
gtcctcaccg tcctgcacca ggactggctg aatggcaagg agtacaagtg caaggtctcc    300
aacaaagccc tcccagcccc catcgagaaa accatctcca aagccaaagg gcagccccga    360
gaaccacagg tgtacaccct gcccccatcc cgggatgagc tgaccaagaa ccaggtcagc    420
ctgacctgcc tggtcaaagg cttctatccc agcgacatcg ccgtggagtg ggagagcaat    480
gggcagccgg agaacaacta caagaccacg cctcccgtgc tggactccga cggcccttc     540 ttcctctaca gcaagctcac cgtggacaag agcaggtggc agcaggggaa cgtcttctca    600
tgctccgtga tgcatgaggc tctgcacaac cactacacgc agaagagcct ctccctgtct    660
ccgggtaaa                                                            669

<210> SEQ ID NO 13
<211> LENGTH: 22
<212> TYPE: PRT
<213> ORGANISM: Homo sapiens

<400> SEQUENCE: 13

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 14
<211> LENGTH: 66
<212> TYPE: DNA
<213> ORGANISM: Homo sapiens

<400> SEQUENCE: 14
atggacatgc gggttccagc ccagcttctc ggacttctgc tgttgtggct gcgcggagca     60
cggtgc                                                                66
```

```
<210> SEQ ID NO 15
<211> LENGTH: 1432
<212> TYPE: DNA
<213> ORGANISM: artificial sequence
<220> FEATURE:
<223> OTHER INFORMATION: full length sequence of heavy chain

<400> SEQUENCE: 15
gagtcgacat ggagttcgga ctcagttggc tgttcctggt ggccatcctg aagggtgtgc      60
agtgtgaagt ccagctggtc gagagcggtg gcgggctggt gcaacccggt ggatcactgc     120
ggctcagctg cgctgctagt ggctttccct tctctaacca ctggatgaat tgggtccggc     180
aggctccagg aaagggtctg gagtgggtgg gtgagatcag gagtaagtct atgaactccg     240
ccacacacta tgctgaaagc gtgaaagggc gcttcacaat ctctagagac gattcaaaga     300
actctctgta cctgcagatg aacagtctga aacagagga ccgctgtg tattactgtg        360 ctcggaacga ctacggtgca gcttacgacc actggggcca aggtacactg gtcaccgtct     420
cgagtgcctc caccaagggc ccatcggtct tccccctggc accctcctcc aagagcacct     480 ctggggggcac agcggccctg ggctgcctgg tcaaggacta cttccccgaa ccggtgacgg    540
tgtcgtggaa ctcaggcgcc ctgaccagcg gcgtgcacac cttcccggct gtcctacagt     600
cctcaggact ctactccctc agcagcgtgg tgaccgtgcc ctccagcagc ttgggcaccc     660
agacctacat ctgcaacgtg aatcacaagc ccagcaacac caaggtggac aagagagttg     720
agcccaaatc ttgtgacaaa actcacacat gcacatgccc accgtgccca gcacctgaac     780
tcctgggggg accgtcagtc ttcctcttcc cccaaaaacc caaggacacc ctcatgatct     840
cccggacccc tgaggtcaca tgcgtggtgg tggacgtgag ccacgaagac cctgaggtca     900
agttcaactg gtacgtggac ggcgtggagg tgcataatgc caagacaaag ccgcgggagg     960
agcagtacaa cagcacgtac cgtgtggtca gcgtcctcac cgtcctgcac caggactggc    1020
tgaatggcaa ggagtacaag tgcaaggtct ccaacaaagc cctcccagcc cccatcgaga    1080
aaaccatctc caaagccaaa gggcagcccc gagaaccaca ggtgtacacc ctgcccccat    1140
cccgggatga gctgaccaag aaccaggtca gcctgacctg cctggtcaaa ggcttctatc    1200
ccagcgacat cgccgtggag tgggagagca atgggcagcc ggagaacaac tacaagacca    1260
cgcctcccgt gctggactcc gacggccct tcttcctcta cagcaagctc accgtggaca    1320
agagcaggtg gcagcagggg aacgtcttct catgctccgt gatgcatgag gctctgcaca    1380
accactacac gcagaagagc ctctccctgt ctccgggtaa atagtctaga gc             1432

<210> SEQ ID NO 16
<211> LENGTH: 471
<212> TYPE: PRT
<213> ORGANISM: artificial sequence
<220> FEATURE:
<223> OTHER INFORMATION: full length sequence of heavy chain

<400> SEQUENCE: 16

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Pro Phe
        35                  40                  45

Ser Asn His Trp Met Asn Trp Val Arg Gln Ala Pro Gly Lys Gly Leu
    50                  55                  60

Glu Trp Val Gly Glu Ile Arg Ser Lys Ser Met Asn Ser Ala Thr His
```

```
                65                  70                  75                  80
Tyr Ala Glu Ser Val Lys Gly Arg Phe Thr Ile Ser Arg Asp Asp Ser
                    85                  90                  95
Lys Asn Ser Leu Tyr Leu Gln Met Asn Ser Leu Lys Thr Glu Asp Thr
                100                 105                 110
Ala Val Tyr Tyr Cys Ala Arg Asn Asp Tyr Gly Ala Ala Tyr Asp His
                115                 120                 125
Trp Gly Gln Gly Thr Leu Val Thr Val Ser Ser Ala Ser Thr Lys Gly
            130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
                180                 185                 190
Pro Ala Val Leu Gln Ser Ser Gly Leu Tyr Ser Leu Ser Ser Val Val
                195                 200                 205
Thr Val Pro Ser Ser Ser Leu Gly Thr Gln Thr Tyr Ile Cys Asn Val
            210                 215                 220
Asn His Lys Pro Ser Asn Thr Lys Val Asp Lys Arg Val Glu Pro Lys
225                 230                 235                 240
Ser Cys Asp Lys Thr His Thr Cys Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
                275                 280                 285
Asp Val Ser His Glu Asp Pro Glu Val Lys Phe Asn Trp Tyr Val Asp
            290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
                355                 360                 365
Glu Pro Gln Val Tyr Thr Leu Pro Pro Ser Arg Asp Glu Leu Thr Lys
            370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Pro Phe Phe Leu Tyr Ser
                420                 425                 430
Lys Leu Thr Val Asp Lys Ser Arg Trp Gln Gln Gly Asn Val Phe Ser
                435                 440                 445
Cys Ser Val Met His Glu Ala Leu His Asn His Tyr Thr Gln Lys Ser
            450                 455                 460
Leu Ser Leu Ser Pro Gly Lys
465                 470

<210> SEQ ID NO 17
<211> LENGTH: 1432
```

```
<212> TYPE: DNA
<213> ORGANISM: artificial sequence
<220> FEATURE:
<223> OTHER INFORMATION: full length sequence of heavy chain

<400> SEQUENCE: 17
gagtcgacat ggagttcgga ctcagttggc tgttcctggt ggccatcctg aagggtgtgc      60
agtgtgaagt ccagctggtc gagagcggtg gcgggctggt gcaacccggt ggatcactgc     120
ggctcagctg cgctgctagt ggcttttccct tctctaacca ctggatgaat tgggtccggc    180
aggctccagg aaagggtctg gagtgggtgg gtgagatcag gagtaagtct atgaactccg     240
ccacacacta tgctgaaagc gtgaaagggc gcttcacaat ctctagagac gattcaaaga    300
actctctgta cctgcagatg aacagtctga aacagagga caccgctgtg tattactgtg     360
ctcggaacgt cgacggtgca ccttacgacc actggggcca aggtacactg gtcaccgtct    420
cgagtgcctc caccaagggc ccatcggtct tccccctggc accctcctcc aagagcacct    480
ctgggggcac agcggccctg gctgcctgg tcaaggacta cttccccgaa ccggtgacgg     540
tgtcgtggaa ctcaggcgcc ctgaccagcg gcgtgcacac cttcccggct gtcctacagt    600
cctcaggact ctactccctc agcagcgtgg tgaccgtgcc ctccagcagc ttgggcaccc    660
agacctacat ctgcaacgtg aatcacaagc ccagcaacac caaggtggac aagagagttg    720
agcccaaatc ttgtgacaaa actcacacat gcacatgccc accgtgccca gcacctgaac    780
tcctgggggg accgtcagtc ttcctcttcc cccaaaaacc caaggacacc ctcatgatct    840
cccggacccc tgaggtcaca tgcgtggtgg tggacgtgag ccacgaagac cctgaggtca    900
agttcaactg gtacgtggac ggcgtggagg tgcataatgc caagacaaag ccgcgggagg    960
agcagtacaa cagcacgtac cgtgtggtca gcgtcctcac cgtcctgcac caggactggc   1020
tgaatggcaa ggagtacaag tgcaaggtct ccaacaaagc cctcccagcc cccatcgaga   1080
aaaccatctc caaagccaaa gggcagcccc gagaaccaca ggtgtacacc ctgcccccat   1140
cccgggatga gctgaccaag aaccaggtca gcctgacctg cctggtcaaa ggcttctatc   1200
ccagcgacat cgccgtggag tgggagagca atgggcagcc ggagaacaac tacaagacca   1260
cgcctcccgt gctggactcc gacggcccct tcttcctcta cagcaagctc accgtggaca   1320
agagcaggtg gcagcagggg aacgtcttct catgctccgt gatgcatgag gctctgcaca   1380
accactacac gcagaagagc ctctccctgt ctccgggtaa atagtctaga gc            1432

<210> SEQ ID NO 18
<211> LENGTH: 471
<212> TYPE: PRT
<213> ORGANISM: artificial sequence
<220> FEATURE:
<223> OTHER INFORMATION: full length sequence of heavy chain

<400> SEQUENCE: 18

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Pro Phe
        35                  40                  45

Ser Asn His Trp Met Asn Trp Val Arg Gln Ala Pro Gly Lys Gly Leu
    50                  55                  60

Glu Trp Val Gly Glu Ile Arg Ser Lys Ser Met Asn Ser Ala Thr His
65                  70                  75                  80
```

Tyr Ala Glu Ser Val Lys Gly Arg Phe Thr Ile Ser Arg Asp Asp Ser
            85                  90                  95

Lys Asn Ser Leu Tyr Leu Gln Met Asn Ser Leu Lys Thr Glu Asp Thr
        100                 105                 110

Ala Val Tyr Tyr Cys Ala Arg Asn Val Asp Gly Ala Pro Tyr Asp His
            115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Arg Val Glu Pro Lys
225                 230                 235                 240

Ser Cys Asp Lys Thr His Thr Cys Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Pro Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 19
<211> LENGTH: 727
<212> TYPE: DNA
<213> ORGANISM: artificial sequence -continued

```
<220> FEATURE:
<223> OTHER INFORMATION: full length sequence of light chain

<400> SEQUENCE: 19
ctgctagcat ggacatgcgg gttccagccc agcttctcgg acttctgctg ttgtggctgc    60
gcggagcacg gtgcgaaatt gtgctcacac agtcaccaga ctttcagtct gtcacccta   120 aggagaaagt gaccatcact tgcagggcct ctcagttcgt cggctatagt atccactggt   180
accagcagaa acccgatcag tcccctaaac tgctgatcaa gtacgcctct gaatcaaggt   240
caggtgtccc cagtcgattt tctggatcag gatctggtac cgacttcacc ctcaccatca   300
atagcttgga ggccgaggac gctgctacct actactgcca acaaagccac agctggcact   360
ttactttcgg tcagggcacc aaggtcgaga ttaagcgcac agtggccgct ccctcagtgt   420
tcatcttccc accttcagac gagcaactga agagcggcac tgccagcgtc gtgtgtctgc   480
tgaacaactt ctaccccagg gaagctaaag tgcagtggaa agtggataat gctctgcaat   540
ccggcaactc ccaggagtcc gtgaccgagc aggatagtaa ggactccaca tatagcctct   600
caagcacact caccttgagc aaggctgact acgagaagca taaggtgtat gcctgtgaag   660
tgacacatca ggggctctcc agtcctgtga caaagtcctt caaccggggc gaatgctagg   720
aattctc                                                           727
```